United States Patent
Di Carlo et al.

(10) Patent No.: US 8,693,762 B2
(45) Date of Patent: Apr. 8, 2014

(54) INERTIAL PARTICLE FOCUSING FLOW CYTOMETER

(75) Inventors: Dino Di Carlo, Los Angeles, CA (US);
Aydogan Ozcan, Los Angeles, CA (US);
Bahram Jalali, Los Angeles, CA (US);
Soojung Hur, Los Angeles, CA (US);
Henry T. K. Tse, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 241 days.

(21) Appl. No.: 13/231,570

(22) Filed: Sep. 13, 2011

(65) Prior Publication Data

US 2012/0063664 A1 Mar. 15, 2012

Related U.S. Application Data

(60) Provisional application No. 61/382,825, filed on Sep. 14, 2010.

(51) Int. Cl.
*G06K 9/00* (2006.01)

(52) U.S. Cl.
USPC .......................................... 382/133; 382/134

(58) Field of Classification Search
None
See application file for complete search history.

(56) References Cited

U.S. PATENT DOCUMENTS

| | | | | |
|---|---|---|---|---|
| 7,695,683 B2 * | 4/2010 | Quan et al. | ..................... | 382/100 |
| 7,792,345 B2 * | 9/2010 | Taylor et al. | .................. | 382/128 |
| 8,208,138 B2 * | 6/2012 | Papautsky et al. | ............ | 356/335 |
| 2007/0090166 A1 * | 4/2007 | Takayama et al. | ............ | 228/101 |
| 2009/0014360 A1 * | 1/2009 | Toner et al. | .................... | 209/208 |
| 2010/0021984 A1 | 1/2010 | Edd et al. | | |

FOREIGN PATENT DOCUMENTS

WO WO 2008/130977 10/2008

OTHER PUBLICATIONS

Cheung, Karen C. et al., Microfluidic Impedance-Based Flow Cytometry, Cytometry Part A, 77A: 648-666, 2010.
Di Carlo, Dino, Inertial Microfluidics, Lab Chip, 2009, 9, 3038-3046.
Goda, K. et al., Serial time-encoded amplified imaging for real-time observation of fast dynamic phenomena, Nature, vol. 458, Apr. 30, 2009, doi:10.1038, nature07980; 1145-4450.
Hsieh, H. Ben et al., High speed detection of circulating tumor cells, Biosensors and Bioelectronics, 21 (2006) 1893-1899.
Hur, Soojung Claire et al., Sheathless inertial cell ordering for extrement throughput flow cytometry, Lab Chip, 2010, 10, 274-280.
Su, Ting-Wei et al., High-Throughput Lensfree Imaging and Characterization of a Heterogeneous Cell Solution on a Chip, Biotechnology and Bioengineering, vol. 102, No. 3, Feb. 15, 2009, 856-868.

(Continued)

*Primary Examiner* — Manav Seth
(74) *Attorney, Agent, or Firm* — Vista IP Law Group LLP

(57) ABSTRACT

A flow cytometry system includes an inertial particle focusing device including a plurality of substantially parallel microchannels formed in a substrate, each microchannel having a width to height ratio in the range of 2:3 to 1:4, an analyzer disposed adjacent the inertial particle focusing device such that the analyzer is configured to detect a characteristic of particles in the inertial particle focusing device, and a controller connected to the analyzer and configured to direct the detection of the characteristic of the particles.

28 Claims, 11 Drawing Sheets

(56) References Cited

OTHER PUBLICATIONS

Bhagat, A.A.S. et al., Enhanced particle filtration in straight microchannels using shear-modulated inertial migration, Phys. Fluids 20, 10 1702-4(2008).
Hsieh, H. et al., High speed detection of circulating tumor cells, Biosensors and Bioelectronics, vol. 21, pp. 1893-1899, 2006.
Kim, Y.R. et al., Isovolumetric sphering of erythrocytes for more accurate and precise cell volume measurement by flow cytometry, Cytometry 3, 419-427(1983).
Kim, Y.W. et al., The lateral migration of neutrally-buoyant spheres transported through square microchannels, Journal of Micromechanics and Microengineering 18, 065015 (2008).
Inamuro, T. et al., Flow between parallel walls containing the lines of neutrally buoyant circular cylinders, International Journal of Multiphase Flow 26, 1981-2004 (2000).
Matas, J. et al., Trains of particles in finite-Reynolds-number pipe flow, Phys. Fluids 16, 4192-4195 (2004).
Matas, J. et al., Inertial migration of rigid spherical particles in Poiseuille flow, Journal of Fluid Mechanics 515, 171-195 (2004).
Oakey, J. et al., Particle Focusing in Staged Inertial Microfluidic Devices for Flow Cytometry, Anal. Chern, vol. 82, pp. 3862-3867. (2010).
Segre, G. et al., Radial Particle Displacements in Poiseuille Flow of Suspensions, Nature 189, 209-210(1961).
Siena, S. et al. Flow cytometry for clinical estimation of circulating hematopoietic progenitors for autologous transplantation in cancer patients, Blood 11, 400-409 (1991).
Su T. et al., High-throughput lensfree imaging and characterization of a heterogeneous cell solution on a chip, Biotechnology and Bioengineering, vol. 102, pp. 856-868, 2009.
Yan, Y. et al., Hydrodynamic interaction of two particles in confined linear shear flow at finite Reynolds number, Phys. Fluids 19, 113305-12 (2007).
Landay, A. et al., Application of flow cytometry to the study of HIV infection, Aids 4, 479-497 (1990).
Altendorf, E. et al., Optical flow cytometry utilizing microfabricated silicon flow channels, SPIE vol. 2678, pp. 267-276 (1996).
Ateya, J. E. et al., The good, the bad, and the tiny: a review of microflow cytometry, Anal Bioanal Chem (2009) 391:1485-1498.
Di Carlo, D. et al., Continuous inertial focusing, ordering, and separation of particles in microchannels, PNAS, vol. 48, No. 104, pp. 19892-18897 (Nov. 27, 2007).
Di Carlo, D. et al., Equilibrium Separation and Filtration of Particles Using Differential Intertial Focusing, Anal. Chem. 2008, 80, 2204-2211.
Di Carlo D. et al., Particle Segregation and Dynamics in Confined Flows, PRL. 102, Mar. 2009, pp. 094503-4.
Chun, B. et al., Inertial migration of neutrally buoyant particles in a square duct: An investigation of multiple equilibrium positions, Physics of Fluids, vol. 18, Mar. 2006, pp. 031704-4.
Edd, J.F. et al., Controlled encapsulation of single-cells into monodisperse picolitre drops, Lab on a Chip, vol. 8, pp. 1262-1264 (2008).
Faivre, M. et al., Geometrical focusing of cells in a microfluidic device: An approach to separate blood plasma, Biorcheology 43 (2006) 147-159.
Golden, J. P. et al., Multi-wavelength microflow cytometer using groove-generated sheath flow, Lab on a Chip, vol. 9, pp. 1942-1950 (2009).
Gossett, D. R. et al., Particle Focusing Mechanisms in Curving Confined Flows, Anal. Chem, 81, 8459-8465 (2009).
Holmes, D. et al., Leukocyte analysis and differentiation using high speed microfluidic single cell impedance cytometry, Lab on a Chip, vol. 9, pp. 2881-2889 (2009).
Huh, D. et al., Microfluidics for flow cytometric analysis of cells and particles, Physiol. Meas. vol. 26, R73-R98 (2005).
Mao, X. et al., Single-layer planar on-chip flow cytometer using microfluidic drifting based three-dimensional (3D) hydrodynamic focusing, Lab on a Chip, vol. 9, pp. 1583-1589 (2009).
McKenna, B. K. et al., 384-Channel parallel microfluidic cytometer for rare-cell screening, Lab on a Chip, vol. 9, pp. 305-310 (2009).
Simmonnet, C. et al., High-Throughput and High-Resolution Flow Cytometry in Molded Microfluidic Devices, Anal. Chem. vol. 78, pp. 5653-5663 (2006).
Chung, T.D. et al., Recent advances in miniaturized microfluidic flow cytometry for clinical use, Electrophoresis, vol. 28, pp. 4511-4520 (2007).

\* cited by examiner

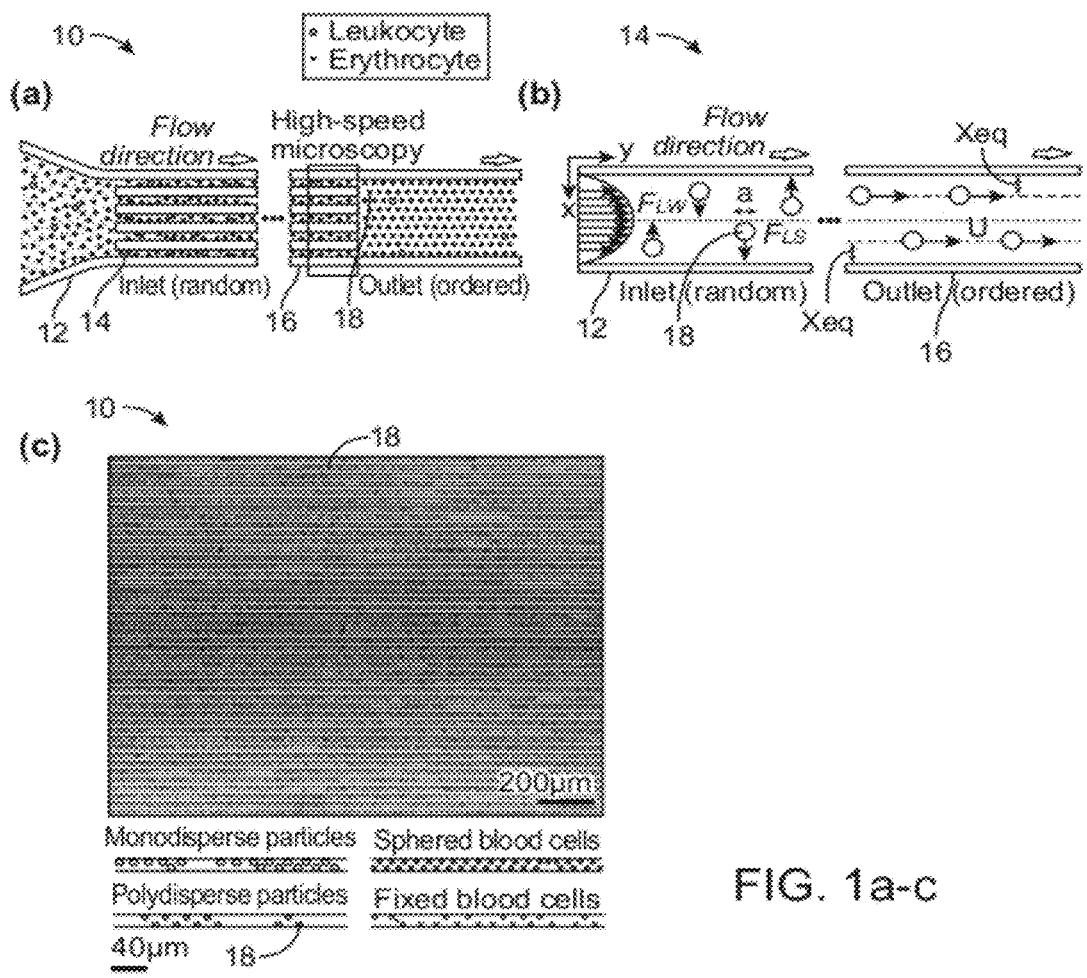
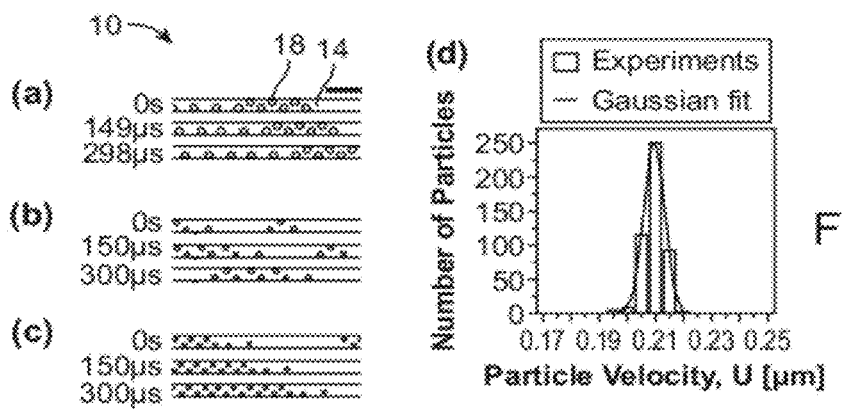
FIG. 1a-c
FIG. 2a-d

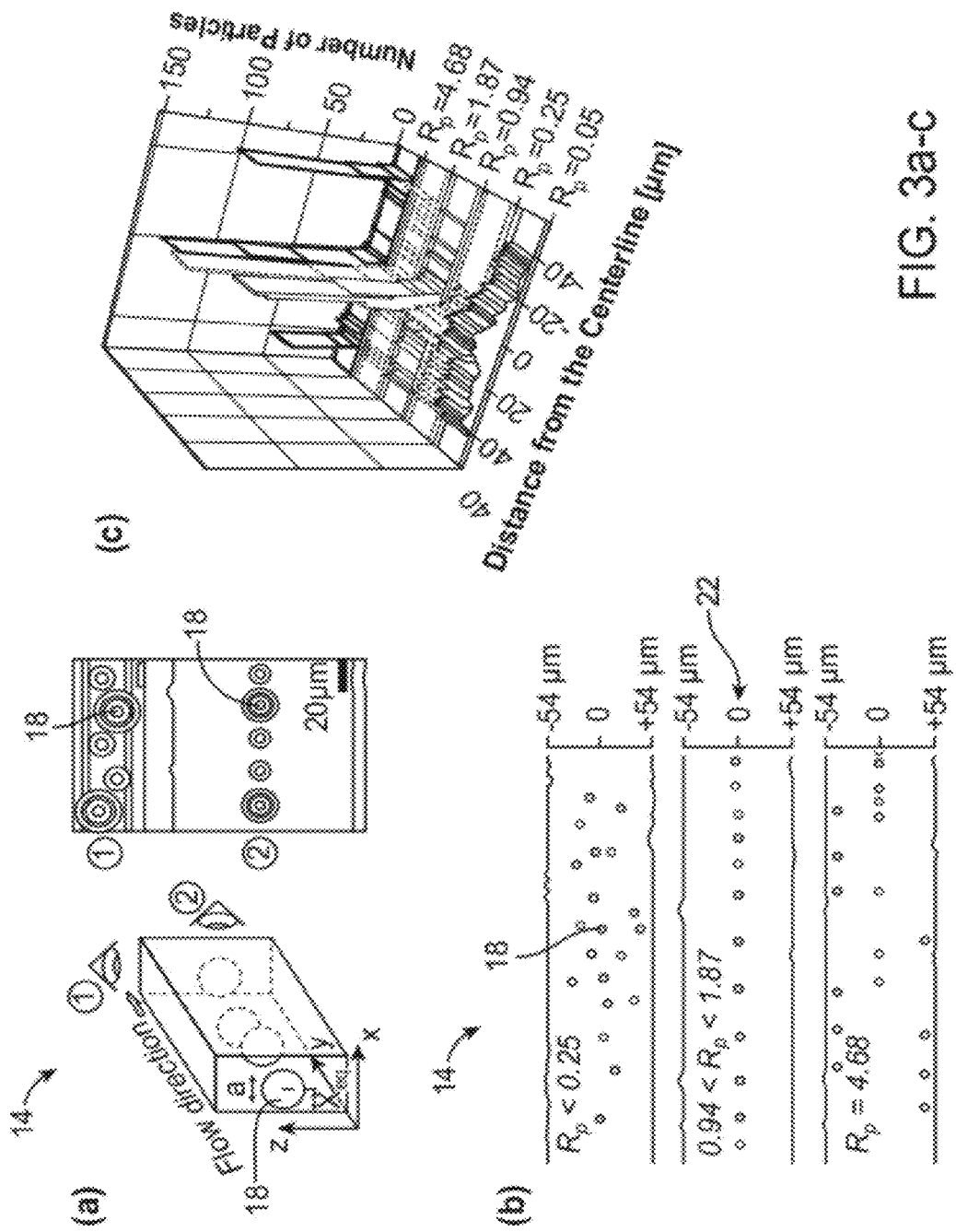
FIG. 3a-c

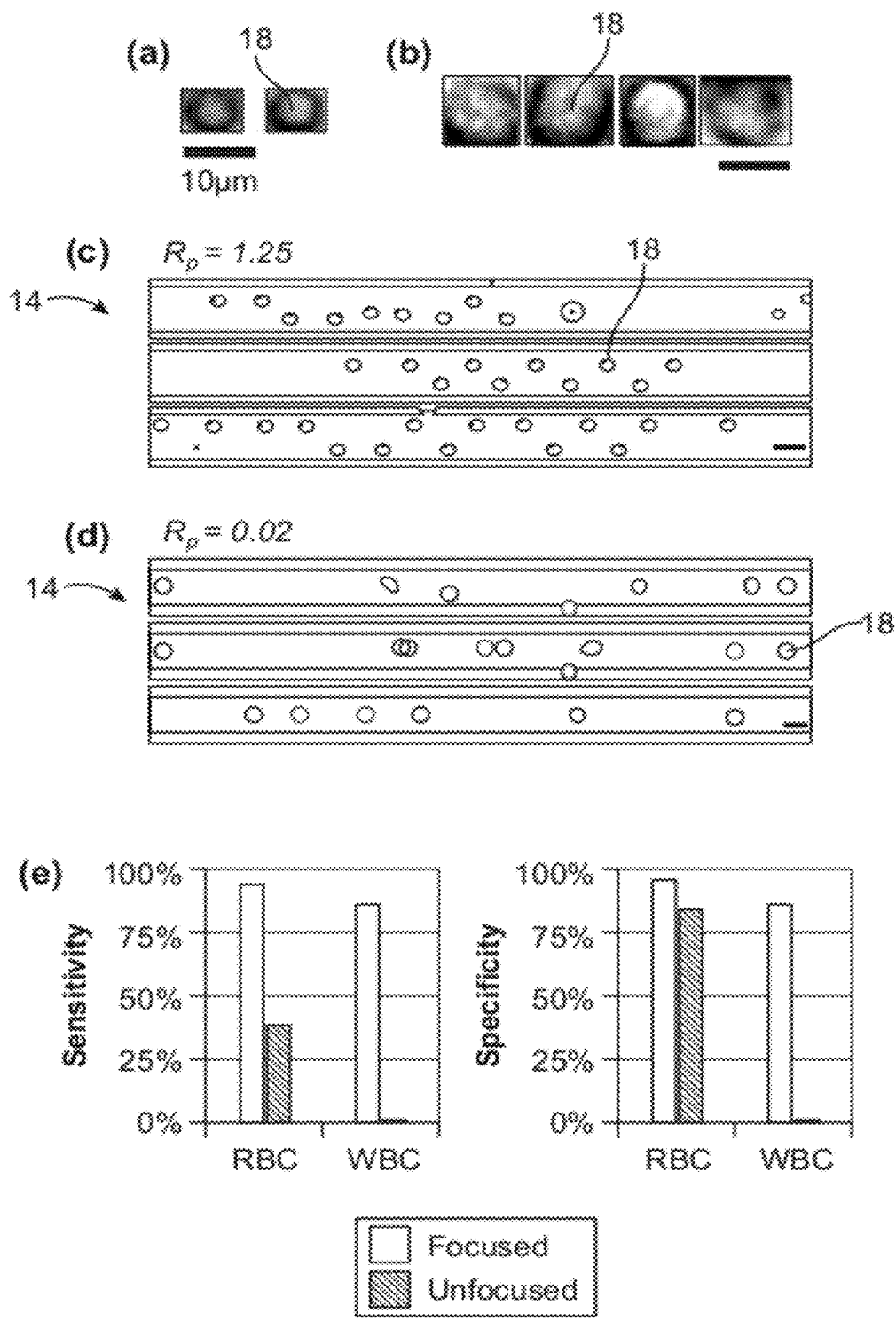
FIG. 4a-e

Ratio of WBC to RBC, sensitivity, and specificity values per sample.

| Sample | Total Detected | | WBC/RBC Ratio | Sensitivity | | Specificity | |
|---|---|---|---|---|---|---|---|
| | RBC | WBC | | RBC | WBC | RBC | WBC |
| Blood Smear | 15,125 | 15 | 0.0010 | - | - | - | - |
| Sample #1 | 4896 | 14 | 0.0028 | 92% | 82% | 95% | 86% |
| Sample #2 | 3098 | 7 | 0.0023 | 95% | 89% | 98% | 90% |
| Total | 7994 | 24 | 0.0025 | 94% | 86% | 97% | 88% |

Fig. 5

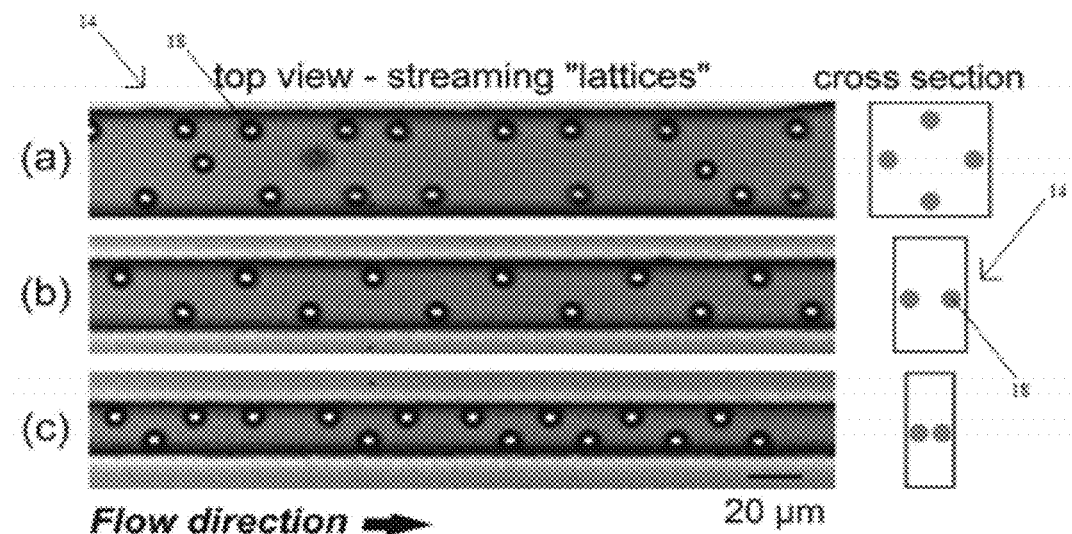
Figs. 6a-c
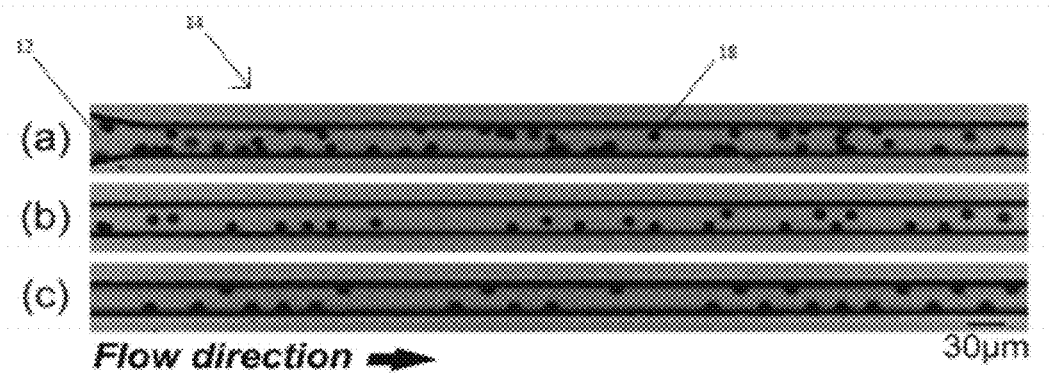
Figs. 7a-c

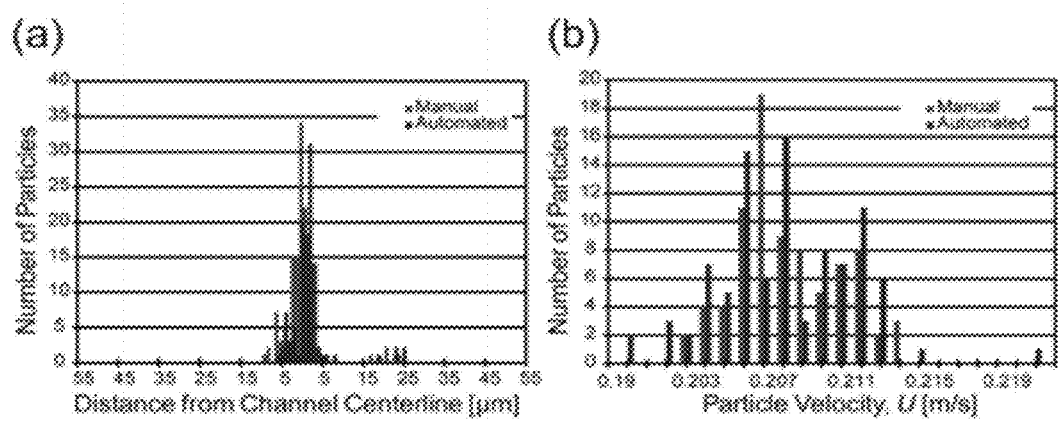
Figs. 8a-b

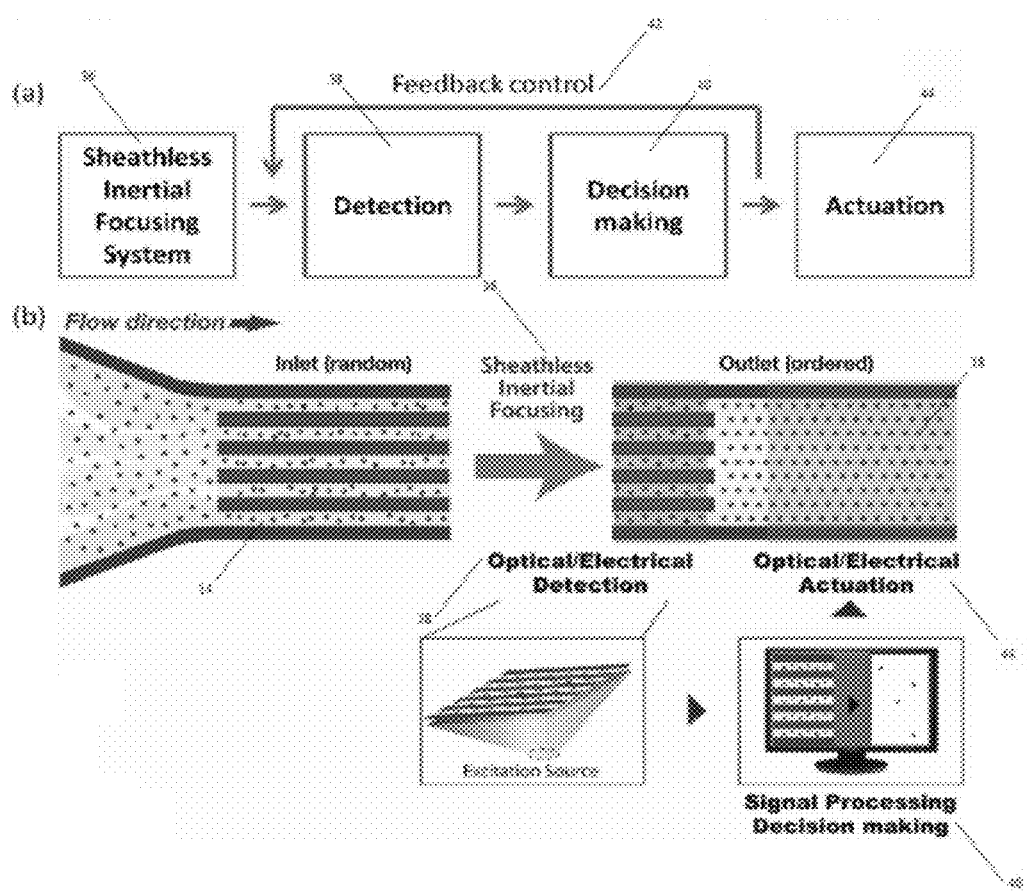
Figs. 12a-b

INERTIAL PARTICLE FOCUSING FLOW CYTOMETER

RELATED APPLICATION

This Application claims priority to U.S. Provisional Patent Application No. 61/382,825 filed on Sep. 14, 2010. Priority is claimed pursuant to 35 U.S.C. §119. The above-noted Patent Application is incorporated by reference as if set forth fully herein.

STATEMENT REGARDING FEDERALLY SPONSORED RESEARCH AND DEVELOPMENT

This invention was made with Government support under 0930501, awarded by the National Science Foundation. The Government has certain rights in the invention.

FIELD OF THE INVENTION

The field of the invention generally relates to systems used to separate, sort, count, and examine particles or cells. More particularly, the invention relates to microfluidic-based flow cytometers.

BACKGROUND

Rapid and accurate differentiation of cell types within a heterogeneous solution is a challenging but important task for various applications in biological research and medicine. Flow cytometry is the gold standard in cell analysis and is regularly used for blood analysis (i.e., complete blood counts (CBC)) to determine general patient health, blood diseases, and HIV or AIDs disease progression through quantitative measurement and analysis of common cell populations in patients' blood samples. Flow cytometry, however, lacks sufficient throughput to analyze rare cells in blood or other dilute solutions in a reasonable time period because it is an inherently serial process. Moreover, these systems have high fixed costs, high operating costs (for sheath fluids, lysis buffers, etc.), and lack of portability, which makes them less than ideal for point-of-care or resource limited settings. Further, the complexity of today's flow cytometers requires trained personnel to operate, analyze, and maintain the systems, adding to operating costs.

Analysis of cells within a heterogeneous solution is a challenging but important task for various applications in biological research and medicine including general characterization of cellular protein content, identification of stem cells or tumor cells from dissociated tissue biopsies, and analysis of cell content in blood and other body fluids. Among cell analysis techniques, flow cytometry is most commonly used because of the quantitative data and significant throughputs ($\sim$10,000 cells/s) achievable. Despite the current success of flow cytometry there is still interest in (1) further increasing throughput and, (2) bringing the availability of instruments to the point-of-care. Clinically, flow cytometry is often used for blood analysis (i.e., complete blood counts (CBC)) to determine general patient health, blood diseases, and HIV or AIDs disease progression. Today, a CBC test generally identifies subpopulations of white blood cells (WBCs), red blood cells (RBCs), platelets, hemoglobin, hermatocrit volume, and platelet volume, but does not identify a variety of rare cells (<10,000 cells/mL) that can also be present in blood and potentially clinically useful (e.g. hematopoietic stem cells, endothelial progenitor cells, and circulating tumor cells).

Statistically accurate identification of these cells is not possible in a reasonable time period using standard flow cytometry, especially in a background of $5 \times 10^9$ RBCs/mL, and even if RBCs are lysed to yield a background of $\sim 10^7$ WBCs/ml. The limited throughputs possible in modern clinical bench top flow cytometers and hematology analyzers is due to the serial nature of the cell focusing and interrogation process. For example the gold standard Abbott Cell-Dyn Hematology Analyzer relies on optical scattering and fluorescence intensity measurements for identification and enumeration of blood components based on a sheath-flow hydrodynamic focusing platform. Upon analysis the system requires sequential chemical lysis of WBC and RBC populations to achieve higher specificity. The complexity in cell interrogation and the use of consumable reagents required for operation prevents parallelization for increased throughput required for rare cell detection purposes.

There is also considerable interest in decreasing the cost of flow cytometry and hematology instruments. These systems have high fixed costs (>$30,000), high operating costs (sheath fluids, lysis buffers), and lack of portability, which makes them less than ideal for point-of-care or resource limited settings. Further, the complexity of today's flow cytometers requires trained personnel to operate, analyze, and maintain the systems, further adding to operating costs. Thus a simpler system could reduce healthcare costs while also increasing patient access.

To address these challenges several efforts to miniaturize flow cytometry using microfluidic techniques have been previously explored such that costs are reduced, with the possibility of increased parallelization and throughput. In most cases, the macroscale mechanism of operation including "sheath flows" necessary to focus cells, and laser scatter and fluorescence are translated directly to the microscale with various miniaturization techniques employed to recapitulate the same macroscale performance. The apparent need for a robust, cost effective, flow cytometers have resulted in numerous advances toward miniaturizing flow cytometry to the microscale.

Flow cytometer systems have operated at rates as high as 17,000 cells/s for cell counts that rely on three separate fluid inputs to create the "sheath flow" necessary to focus cells to a single optically interrogated volume. Other flow cytometer systems utilize secondary flow around curving channels for sheath-based 3D hydrodynamic focusing to position cells to a single z-position. Each of these systems are able to achieve highly uniform cell positioning for WBC differentiation with a final throughput of 1,700 cell/s.

Another system includes a microflow cytometer in which the sample fluid was ensheathed and hydrodynamically focused into small interrogated volume ($20 \times 34 \times 30$ μm3) using a microstructured channel with chevron-shaped grooves. This system interrogated cells utilizing an embedded fiber-optic detection system allowing for miniaturization. Still other systems are shealthless microscale cytometer systems, which have the ability to differentiate and count blood components in the randomly dispersed flows. One such system uses laser light scattering techniques to achieve a 3-part WBC differentiation in addition to platelets, and RBC enumeration with a throughput of 1000 cells/s.

Still other systems achieve shealthless cell counts in microchannel flows by using differential impedance spectroscopy for detection, allowing for WBC enumeration and sub-type differentiation, achieving a throughput of 100 cells/s. Yet another system included parallelization of optical cytometry for the purpose of rare cell detection. This system successfully resulted in a 384-channel parallel microfluidic cytometer capable of handling large numbers of unique samples with a rare-cell sensitivity (20~40 positive events in 1000 cells/µl). Although successful for the application of identifying cells expressing parathyroid hormone receptor, the system's low-throughput (1070 cells/s), large footprint (25×50 cm$^2$), and complex confocal laser detection system, may inhibit its adoption as a flow cytometer substitute.

Further increases in throughput in these microscale systems have been challenging, mainly because the methods of cell focusing and optical interrogation are not trivially parallelized, and in the case of sheath flow, requires increases instrument bulk, minimizing the impact of the attempted miniaturization. In order to have a commercially viable impact on rare cell and point-of-care analysis, new systems will have to retain the accuracy but surpass the throughput of current benchtop systems while also being robust, cost efficient and easy to use. Thus there is a need for fundamentally new methods and systems to focus cells and collect data massively in parallel to meet these demands. There is also a need for a high throughput and cost effective flow cytometer.

SUMMARY

In one embodiment, a flow cytometry system includes an inertial particle focusing device including a plurality of substantially parallel microchannels formed in a substrate, each microchannel having a width to height ratio in the range of 2:3 to 1:4, an analyzer disposed adjacent the inertial particle focusing device such that the analyzer is configured to detect a characteristic of particles in the inertial particle focusing device, and a controller connected to the analyzer and configured to direct the detection of the characteristic of the particles. The inertial particle focusing device also includes an inlet connected to the reservoir connected to a proximal end of each microchannel, a reservoir containing particles in fluid and connected to the inlet, and an outlet connected to a distal end of each microchannel. Further, the system may include a pressure source configured to drive the particles in fluid through the inertial particle focusing device and the inlet may include a filter.

In some embodiments, the plurality of substantially parallel microchannels includes 10-1000 microchannels. The plurality of substantially parallel microchannels may include approximately 250 microchannels, although fewer or more could be used. Each microchannel may be substantially rectangular in cross section and may have a width to height ratio of approximately 2:1. The analyzer may be aligned with a short (x) axis of the microchannels. The analyzer may also be disposed relative to the microchannels such that the analyzer is configured to detect the characteristic of particles at a distal end of at least one microchannel. The analyzer may have a field of view sufficiently large to simultaneously detect the characteristic of particles in at least 10 microchannels. In some embodiments, the characteristic is an optical signature or an electrical signature. In other embodiments, the analyzer is configured to capture an image of particles in the inertial particle focusing device.

In some embodiments, each microchannel has width W and the system is configured for use with particles having diameter a, such that a is between 20% and 70% of W. Alternatively or additionally, each microchannel has width W and the system is configured for use with particles having diameter a suspended in fluid having density ρ, maximum velocity $U_m$, and viscosity µ, such that particle Reynolds number, $R_p = \rho U_m a^2/\mu W$, is between 0.3 to 2.

In another embodiment, a method of analyzing particles includes suspending the particles in a fluid, flowing the fluid and particles through an inertial particle focusing device including a plurality of substantially parallel, high-aspect ratio microchannels formed in a substrate, each microchannel having a width to height ratio in the range of 2:3 to 1:4, detecting a characteristic of particles in the inertial particle focusing device, and analyzing the detected characteristic. Optionally, each microchannel has width W, the particles have diameter a, and the fluid having density ρ, maximum velocity $U_m$, and viscosity µ, such that particle Reynolds number, $R_p = \rho U_m a^2/\mu W$, is between 0.3 to 2. In some embodiments, flowing the fluid and particles through an inertial particle focusing device substantially focuses the particles in a z direction, substantially aligns the particles in an x direction, and/or substantially uniformly spaces individual particles in a y direction.

Detecting a characteristic of particles in the inertial particle focusing device may include detecting the characteristic along a short (x) axis of the microchannel. Detecting a characteristic of particles in the inertial particle focusing device may also include detecting the characteristic of particles at a distal end of a microchannel and/or simultaneously detecting the characteristic of particle in portions of at least 10 microchannels. In some embodiments, the characteristic is an optical signature or an electrical signature. In other embodiments, detecting a characteristic includes capturing an image of particles in the inertial particle focusing device.

Additionally, analyzing the detected characteristic may include identifying at least two types of particles. Moreover, identifying at least two types of particles may include identifying visually distinguishable bright-field cell signatures. In some embodiments, each microchannel has width W and the particles have diameter a, such that a is between 20% and 70% of W.

BRIEF DESCRIPTION OF THE DRAWINGS

FIG. 1a is a schematic view of a portion of an inertial particle focusing system according to one embodiment of the invention.

FIG. 1b is a schematic view of particles/cells flowing through a microchannel.

FIG. 1c is a series of five high-speed microscopic images of particles and blood cells flowing through a massively parallel inertial particle focusing device.

FIG. 2a is a series of three time-lapsed high-speed light microscopic images of monodisperse polystyrene beads flowing through microchannels.

FIG. 2b is a series of three time-lapsed high-speed light microscopic images of polydisperse polystyrene beads flowing through microchannels.

FIG. 2c is a series of three time-lapsed high-speed light microscopic images of sphered blood samples flowing through microchannels.

FIG. 2d is a bar graph plotting the number of particles at a particular velocity versus the velocity of monodisperse particles.

FIG. 3a is a schematic of a high aspect ratio straight microfluidic channel with particles flowing therethrough (left) and two high-speed microscopic images of particles in the microchannel obtained from two different viewpoints (right).

FIG. 3b is a series of three high-speed microscopic images of particles in the microchannel of FIG. 3a at various $R_p$ regimes.

FIG. 3c is a 3D histogram illustrating flow speed dependence of particle alignment in the z direction.

FIG. 4a is a series of two bright-field images used as kernels for RBCs.

FIG. 4b is a series of four bright-field images used as kernels for WBCs.

FIG. 4c is a high-speed light microscopic image showing the detection of focused and aligned RBCs and WBCs flowing through a microchannel.

FIG. 4d is a high-speed light microscopic image showing the detection of unfocused RBCs and WBCs flowing through a microchannel with an insufficient $R_p$.

FIG. 4e contains two bar graphs comparing the detection sensitivity and specificity of focused and unfocused cells.

FIG. 5 is a table showing the ratio of WBCs to RBCs, sensitivity, and specificity for test and control samples.

FIGS. 6a-c are high-speed microscopic images of 10 μm polystyrene particles ordered in 50×50 μm (FIG. 6a), 30×50 μm (FIG. 6b), and 20×50 μm (FIG. 6c) channels.

FIGS. 7a-c are three high-speed microscopic images particles flowing in microchannels. The three high-speed images were taken at the inlet 12 (FIG. 7a), 5 mm downstream (FIG. 7b) and 1 cm downstream (FIG. 7c).

FIGS. 8a and 8b are bar graphs that plot the number of particles versus (a) distance from channel centerline and (b) particle velocity, respectively.

FIGS. 12a-b are a flow chart (a) and a schematic view (b) of the system operation according to still another embodiment of the invention.

DETAILED DESCRIPTION OF THE ILLUSTRATED EMBODIMENTS

Figure 9:
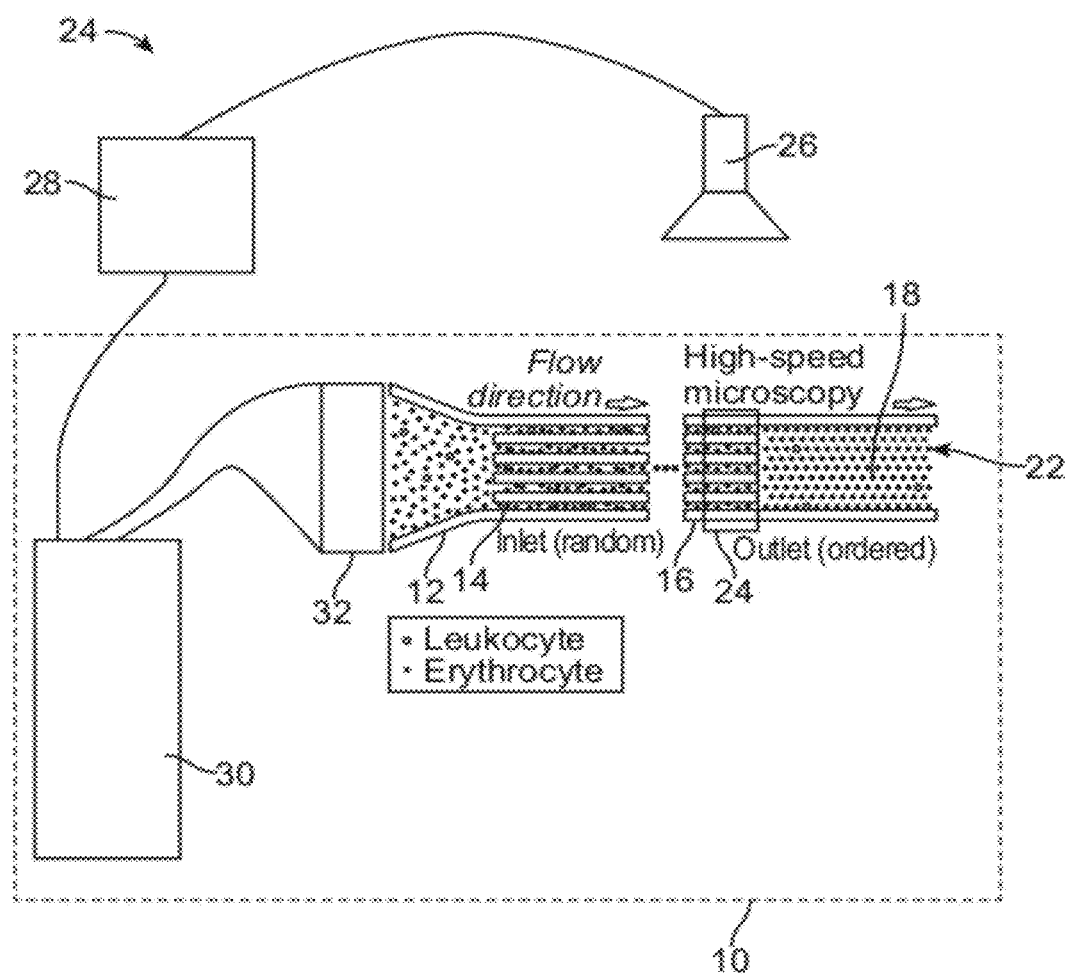
FIG. 9 is a schematic view of a flow cytometry system 24 according to another embodiment of the invention.

In one embodiment, a sheathless inertial cell ordering microfluidic device 10 is integrated with state of art optical interrogation methods, such as the lens-free holographic on-chip imaging technique (FIG. 10) and serial time encoded amplified imaging technique (FIGS. 11a-b) to provide a compact and cost-effective platform for extreme throughput single cell analysis by complementing the limits of current flow cytometry. These optical interrogation methods are described below with reference to FIGS. 10 and 11a-b. This device 10 has potential to enable a complete whole blood count with 200 fold higher analysis speed and great accuracy.

Microchannel-dependent inertial effects (massively parallel) allow for label- and sheath-free parallel flow cytometry with extreme throughput. In one embodiment, a microfluidic device 10 consists of 256 high aspect (W=16 μm, H=37 μm) parallel channels 14, each channel 14 having a length of 2.5 cm. Such a microfluidic device 10 can have a sample rate up to 1 million cells/s, only limited by the field of view of the associated high-speed imaging optical interrogation method. The particles or cells 18 flowing through the channels 14 are focused to one uniform z-position with uniform downstream velocity to reduce the probability of overlap and out-of-focus blur, and to provide similar cell signature images for accurate detection and analysis. Precisely ordered particle and cell lattices travel with uniform velocity, $U_{ave}$=0.208±0.004 m/s at operating flow rates described below. Moreover, using micro channels with inverted aspect ratio (W:H~2:1), uniform z-plane positions of particle lattices localized to the centerline (SD=±1.81 μm). While a microchannel aspect ratio of ~2:1 is used in this embodiment, aspect ratios in the range of 3:2 to 4:1 can also be used.

Automated RBC and sub-population leukocyte counts on diluted whole blood using a system according to an embodiment of the invention achieved a counting sensitivity of 94% and 86%, respectively, with specificity of 97% and 88% respectively, as compared to visual inspection of raw images. Further, sensitivity increased 59% when comparing uniformly ordered particles to randomly dispersed particles for automated cell identification purposes. Because no additional external forces (e.g. optical, magnetic, electrical) are required to create ordered streams of cells, this system has the potential for future applications in cost-effective and simple hematology or rare cell analysis platforms with extreme throughput capabilities when integrated with suitable large field-of view imaging or interrogation methods.

The device design, fabrication, and operation of a novel parallel microfluidic focusing system are described herein. The system is also validated with image-based blood cell counts. The sheathless device is constructed with a single inlet 12 splitting into 256 channels 14 in which cells 18 are positioned and spatially ordered by inertial effects to well defined focal planes in all parallel channels 18. The high uniformity in position and reduction in overlap of cells allows easier operation, detection and differentiation of cell types at higher cell concentrations than traditional flow cytometers.

The device operates with 1% v/v diluted blood at an overall flow rate Q=2.5 ml/min resulting in cell velocities of 0.42 m/s and total throughputs of ~1 million cells/s. Using conventional microscopic analysis and high-speed imaging of a 450×330 μm² field of view yields an analyzed throughput of ~1 million cells/s for 10 channels, with the capabilities of new wide-field imaging techniques even higher throughputs can be expected. Thus, taking advantage of microscale physics, the presented system and method provide improved throughput over traditional flow cytometry in a disposable platform with less logistical requirements, potentially enabling both rare cell and point-of-care applications for flow cytometry.

Theoretical Background.

Inertial effects in microfluidic systems focus and order particles and cells continuously without external forces. In brief, there are two inertial lift forces, namely a wall effect lift, $F_{LW}$, and a shear-gradient lift, $F_{LS}$ (see FIG. 1b) inducing lateral migration of particles in confined flow and creating distinct inertial lift equilibrium positions at finite Reynolds numbers. Moreover, it has been found that the critical channel length, $L_f$, that is required for particle focusing, can be calculated by balancing the shear-gradient lift force with Stokes drag. $L_f$ can be calculated as follows:

$$L_f = \frac{\pi \mu W^2}{\rho U_m a^2 f_L},$$

where W is the channel width in the direction of particle migration. μ and ρ are the fluid viscosity and density, $U_m$ is the maximum channel velocity, a is the particle/cell diameter and $f_L$ is the average lift coefficient that varies from ~0.02-0.05 depending on the aspect ratio (H/W) from 2 to 0.5.

In these finite-inertia channel systems, cells and particles in confined flow focus to distinct equilibrium positions corresponding with channel geometry. Lateral particle migration to an annulus was first observed in centimeter scale pipes. While particles flowing through square or rectangular channels were also found to focus to 4 distinct equilibrium positions corresponding to the channel fold symmetry. (FIG. 6a). Increasing the channel aspect ratio removes unstable focusing positions at short faces and retains the two equilibrium positions centered at the long face of the channel (FIGS. 6b and c).

Certain parameters encourage sheathless inertial focusing, for instance: individual channels aspect ratios (ratio between channel width to height) equal or similar to 2; particle diameter between 20% and 70% of channel width; and particle Reynolds number, $R_p = \rho U_m a^2/\mu W$, ranging from 0.3 to 2. Here, $\rho$, $U_m$, $\mu$ are density, maximum velocity, viscosity of the fluid, respectively, and a and W are particle diameter and channel width, respectively.

Particles flowing in these channels also order in the direction of flow with preferred inter-particle spacing when the particle Reynolds number is on the order of 1. This effect reduces particle overlap errors, important for flow cytometry applications. The inter-particle spacing has been observed in millimeter scale pipe flow as single trains 22 while in rectangular microchannels staggered double trains 22 were found. These observations were confirmed with simulations of cylinders flowing through infinite plates with finite Reynolds number. For example, high aspect channels (H/W>2) focus particles to two positions with controlled inter-particle spacing and tight z-position for applications in sheathless flow cytometry.

Device Fabrication.

Microfluidic chips with 256 parallel straight channels, wherein each individual channel width was 16 μm, were cast of PDMS (Sylgard 184™, Dow Corning) using a photolithographically fabricated master mold. For mold fabrication, a 4" silicon wafer was spin-coated with a 37 μm thick layer of a negative photoresist (KMPR 1050™, Microchem), exposed to UV-light through a designed Cr-photomask and developed. Eighty grams of PDMS base and crosslinker mixture was poured onto the mold and degassed for 30 min to remove all trapped bubbles. The degassed mold was then placed onto a leveled horizontal surface in a 65° C. oven for 3 hours to complete the curing. The cured PDMS cast was separated from the mold and the inlet 12 and outlet 16 were punched with a pin vise (Pin vise set A, Technical Innovations Inc.). The punched PDMS chip was bonded to a slide glass by exposing both PDMS and a slide glass surfaces to air plasma (Plasma Cleaner™, Harrick Plasma) to enclose the microfluidic chip with 256 parallel channels 14 and a reservoir.

Particle Suspensions.

Monodisperse polystyrene particles (a=9.9 μm, Duke Scientific Corporation) were suspended in deionized water with 3% w/v Tween 80 (Fisher Chemical) to reach a final particle concentration of 3% v/v. In addition, polydisperse polystyrene particles ($a_{ave}$=7.9 μm, size distribution <20% CV, Duke Scientific Corporation) were diluted to 1% v/v in the same Tween 80 solutions.

Blood Sample Dilution and Fixation.

Blood cells were suspended in Dulbecco's modified eagle's medium (DMEM) with 5% fetal bovine serum (FBS) to reach desired final cell concentrations. DMEM with 5% FBS will hereinafter be referred to as media. Both blood sample and media were placed in a water bath maintained at 37° C. for 30 min prior to the mixing in order to minimize cell morphology changes. For processing fixed blood cells, 1% v/v of Glutaraldehyde (Fisher Scientific) was added to the diluted blood sample to polymerize live cells so that their shape is preserved. After 15 min incubation, the fixed blood samples were washed three times with media to minimize forming clumps of polymerized cells.

Sphering Red Blood Cells.

Red blood cells were sphered to enhance the contrast between red blood cells and white blood cells for image analysis. Red blood cells were sphered by following the recipe. Sphering agent was prepared by dissolving 1 mg/dl sodium dodecylsulfate in DPBS (260~305 mosm/kg). 80 μl of whole blood was mixed with 40 ml of sphering agent. The mixture was centrifuged at 2500 rpm for 3 min and the supernatant was aspirated to have final cell concentrations of 1 or 5% v/v.

Staining a Blood Smear.

Blood sample was smeared and stained with the Wright-Giemsa stain (Sigma-Aldrich, Accustain®) by following the standard staining protocol. In brief, smeared and thoroughly dried blood films on a slide were placed in Wright-Giemsa stain for 30 seconds and excessive stain was washed from the sample by placing the same slide in deionized water for 10 min without agitation. The slide was briefly rinsed in running deionized water followed by air drying before evaluation. Number of red and white blood cells was counted as from microscopic images taken at randomly picked location on the smeared sample and compared with the counting result from the automated image analysis.

Massively Parallel Inertial Focusing.

The parallel ordering capability of the microfluidic chip was demonstrated with mono/polydisperse polystyrene beads as well as diluted fresh, fixed, or sphered whole blood samples. The solutions containing microparticles were injected into the device with a syringe pump (Harvard Apparatus, PHD 20000™) to sustain the overall flow rate, Q, ranging between 5.5 μl/min and 2.5 ml/min. The loaded syringe was connected to ⅟₃₂×0.02" PEEK tubing (Upchurch Scientific) by a ½" Luer stub (Instech Solomon) and tubing was secured in the punched inlet 12 and outlet 16 of the microfluidic device 10. It was possible to create well-ordered particle/cell streams evenly through more than 200 channels 14 in parallel.

Uniform z-Plane Measurements of Well-Ordered Particles.

To verify that focused particles/cells 18 were in the same z-plane, the monodisperse particle suspension was injected through a single straight channel with inverted aspect ratio (i.e., W>H and W:H≈2:1). $R_p$ was varied from 0.05 to 4.68 to determine the optimum condition yielding uniform z-positions. While a microchannel aspect ratio of ~2:1 is used in this embodiment, aspect ratios in the range of 3:2 to 4:1 can also be used.

High Speed Imaging.

High-speed microscopic images of particle/cell trains 22 were recorded downstream (See FIGS. 6a-c) using a Phantom™ v7.3 high speed camera (Vision Research Inc.) and Phantom Camera Control™ software. All high speed images were taken using 1 μs exposure time and image intervals were varied according to the flow rate. Particle velocity and focusing position distribution were determined using high-speed microscopy and quantified manually using IrfanView™. Obtained values were compared with those determined with an automated image analysis method implemented in MATLAB for validation of the automated image analysis method (see FIG. 8). The MATLAB script can be found in the supplementary materials to *Sheathless inertial cell ordering for extreme throughput flow cytometry*, Hur, S. C., Tse, H. T. K., Di Carlo, D., Lab on a Chip 2010, 10, 274-280. Both the article and the supplementary materials are incorporated by reference.

Automated Image Analysis.

The analysis of particle velocity, equilibrium position, total particle counts and red and white blood cell identification were performed post-experiment using the abovementioned MATLAB script. Post-processing of the raw images included enhancing images with standard Fourier space filtering techniques. The script allows users to define identification parameters such as size, and matching intensity differential, in order to match to cell types of interest. A subset of the resulting data was then compared to measurements done manually to verify velocity and location accuracy (FIG. 8). Additionally, the total red and white blood cell counts were manually examined to determine sensitivity (false negatives), the ratio of total identified to actual total, and specificity (false positives), the ratio of correctly identified to total identified.

Inertial focusing for parallel cytometry applications is improved by localizing cells and particles to precise z-positions within a flow and ensures uniform velocities. The particles or cells are focused to one uniform z-position to reduce the probability of overlap and out-of-focus blur and provide similar cell signature images for accurate detection and analysis. A stable particle velocity is also preferred such that each cell will have substantially identical residence times within the given field of view yielding substantially identical excitation intensities for laser based interrogation, or yielding the ability to synchronize the frequency of a raster scanning laser, that is used to obtain spatial information about the cell, with cell downstream velocity.

FIGS. 1a-c demonstrate the device working principal. The inertial microfluidic device 10 consists of an inlet 12 with a coarse filter (not shown), 256 parallel straight channels 14 (W=16 µm and H=37 µm), a large reservoir (not shown), and an outlet 16. FIG. 1a is a schematic view of a portion of a system according to an embodiment of the invention, showing an inlet 12 where randomly distributed particles/cells 18 are injected and an outlet 16 where all injected particles/cells 18 are uniformly spaced and flowing with uniform velocity. FIG. 1b is a schematic view of particles/cells 18 in a channel 14, showing two lateral forces, namely wall effect lift, $F_{LW}$, and shear gradient lift force, $F_{LS}$, that particles/cells 18 with diameter, a, experience as they travel through the straight channel region induce lateral migration of particles/cells 18 and focus them at lateral equilibrium positions, $X_{eq}$, at the channel outlet 16, resulting in a uniform particle velocity, U. FIG. 1c is a series of five high-speed microscopic images of particles 16 and blood cells 16 flowing through the massively parallel inertial microfluidic device 10. The coarse filter may be posts or other obstructions across the path of flow that are configured to remove dust or other large particles from the flowing fluid before focusing. The spacing between the posts or obstructions is larger than the largest particle size.

FIGS. 2a-d demonstrate uniform velocity for particles/cells 18 in the inertial particle focusing device 10. FIG. 2a is a series of three time-lapsed high-speed light microscopic images of monodisperse polystyrene beads 18 (a=9.9 µm) flowing through microchannels 14. The scale bar is 20 µm. FIG. 2b is a series of three time-lapsed high-speed light microscopic images of polydisperse polystyrene beads ($a_{ave}$=7.9 µm) flowing through microchannels 14. FIG. 2c is a series of three time-lapsed high-speed light microscopic images of 5% v/v sphered blood samples ($a_{ave}$=6.78 µm) flowing through microchannels 14. FIG. 2d is a bar graph plotting the number of particles 18 at a particular velocity versus the velocity of monodisperse particles 18 analyzed with the automated image analysis script ($U_{ave}$=0.208±0.004 m/s with overall flow rate, Q=1.2 ml/min, $Q_i$=4.7 ul/min per channel, $R_p$=0.9).

FIGS. 3a-c demonstrate the tendency of particles/cells 18 flowing through a high aspect ratio microchannel 14 to migrate to a uniform z-plane. FIG. 3a is a schematic of the inertial focusing particles 18 in a straight microfluidic channel 14 with high aspect ratio (W:H=1:2) (left) and two high-speed microscopic images obtained from two different viewpoints (right). FIG. 3b is a series of three high-speed microscopic images of particles 18 in the microchannel 14 of FIG. 3a at various $R_p$ regimes. FIG. 3c is a 3D histogram illustrating flow speed dependence of particle alignment in the z direction (viewpoint 2 in FIG. 3a). At low flow rates, $R_p$<0.25, flowing particles 18 are randomly distributed while at moderate flow rates, 0.94<$R_p$<1.87, particles 18 aligned into a single train 22. As the flow speed exceeds the optimum flow rate, $R_p$=4.68, particles 18 begin to align at multiple focusing positions in the z-plane.

FIGS. 4a-e show automated image analysis and detection using the abovementioned MATLAB script. FIG. 4a is a series of two bright-field images used as kernels for RBCs. FIG. 4b is a series of four bright-field images used as kernels for WBCs. FIG. 4c is a high-speed light microscopic image showing the detection of focused and aligned RBCs and WBCs flowing through a microchannel 14. FIG. 4d is a high-speed light microscopic image showing the detection of unfocused RBCs and WBCs flowing through a microchannel 14 with an insufficient $R_p$. The RBCs and WBCs detected in FIGS. 4c and 4d are marked with red and blue dots, respectively. The unfocused cells are in multiple z-planes and overlap is apparent in FIG. 4d. FIG. 4e contains two charts comparing the detection sensitivity and specificity of focused and unfocused cells. Scale bars in FIGS. 4a-d are 10 µm.

FIG. 5 is a table showing the ratio of WBCs to RBCs, sensitivity, and specificity for each of two samples ("#1" and "#2") and a manually analyzed control ("Blood Smear").

FIGS. 6a-c demonstrate aspect ratio effects on inertial ordering and focusing. High-speed microscopic images of 10 µm polystyrene particles 18 ordered in 50×50 µm (FIG. 6a), 30×50 µm (FIG. 6b), and 20×50 µm (FIG. 6c) channels 14. Particles 14 are flowing from left to right at U~10 cm/sec. Images are taken 4 cm downstream of the particle inlet 12. Ordering and focusing accuracy is seen to increase with decreasing channel width. Inter-particle distance in the stable ordering lattice is seen to decrease with decreasing channel dimensions.

FIGS. 7a-c are three high-speed microscopic images that show development of inertial ordering in a microchannel 14. The three high-speed images were taken at the inlet 12 (FIG. 7a), 5 mm downstream (FIG. 7b) and 1 cm downstream (FIG. 7c). In FIGS. 7a-c, 10 µm particles 18 flow in a 30×50 µm channel at U~10 cm/sec. At the inlet 12 the particles 18 are randomly distributed. After traveling 5 mm downstream particles 18 have become more ordered and few overlapping particles 18 are observed. After traveling 1 cm downstream in the straight channel 14, equilibrium ordering positions are substantially achieved.

FIGS. 8a and 8b are two bar graphs that plot the number of particles versus (a) distance from channel centerline and (b) particle velocity, respectively. FIGS. 8a and 8b compare manual and automated image analysis results for (a) distance from channel centerline and (b) particle velocity.

FIG. 9 is a schematic view of a flow cytometry system 24 according to another embodiment of the invention. The flow cytometry system 24 includes an inertial particle focusing device 10, an analyzer 26, and a controller 28. The analyzer 26 is configured to capture a characteristic, e.g., an optical or electrical signature, of the particles passing through the inertial particle focusing device 10. As described above, the inertial particle focusing device 10 has a large reservoir 30 connected to an inlet 12, which splits into 256 parallel straight channels 14, which, in turn, coalesce in an outlet 16. The reservoir 30 may include a pump, like a syringe pump, peristaltic pump, pressure source, or other liquid pumping instrument known to those in the art (not shown), to force a fluid containing particles 18 through the channels 14. The inlet 12 may have a filter 32 to prevent debris from entering and clogging the channels 14. Flowing the particles 18 through the channels 14 substantially focuses, aligns, and uniformly spaces the particles 18 in the channel 14 in respective z, x, and y directions. Flowing the particles 18 through the channels 14 also substantially normalizes their velocities through the channel 14 to one value. These particles 18 are most uniform, in position and velocity, in the distal end 34 of the channels 14, before the channels 14 coalesce into the outlet 16. Therefore, the analyzer 26 analyzes the particles at the distal end 34 of the channels 14. The analyzer 26 may be any of the wide-field systems described herein. The flow cytometry system 24 also a controller 28 configured to direct the flow of particles 18 through channels 14, the analysis of the particles, and the processing of the analyzed data. While these functions are performed by a single controller 28 in this embodiment, these functions can be performed by distinct controllers in other embodiments.

Figure 10:
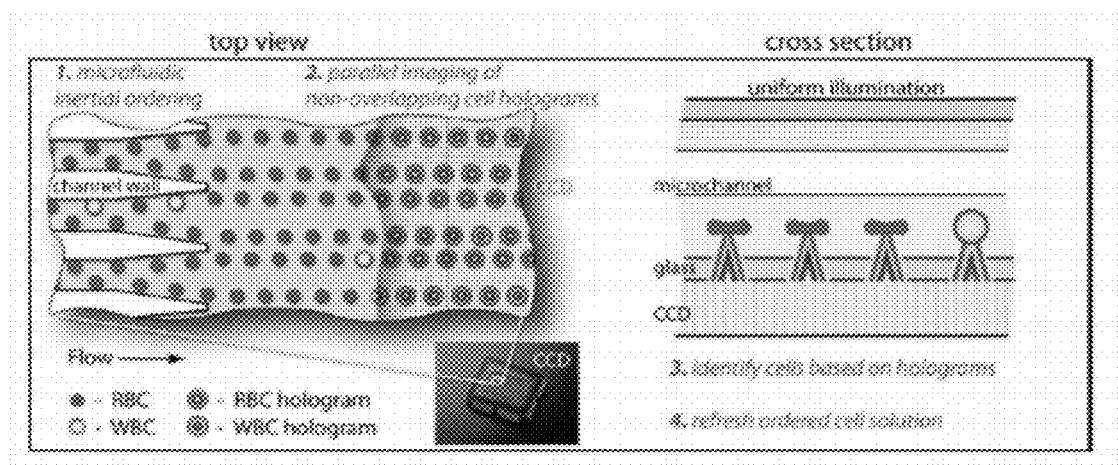
FIG. 10 is a schematic overview of a sheathless, inertial cell ordering microfluidic device based, Lens-less, Ultra wide-field, Cell monitoring Array platform based on Shadow imaging (LUCAS) platform.

FIG. 10 is a schematic overview of a sheathless, inertial cell ordering microfluidic device based, Lens-less, Ultra wide-field, Cell monitoring Array platform based on Shadow imaging (LUCAS). Details regarding the high-throughput imaging platform may be found in Su, S. Seo, A. Edinger, and A. Ozcan, "High-throughput lensfree imaging and characterization of a heterogeneous cell solution on a chip," Biotechnology and Bioengineering, vol. 102, pp. 856-868, 2009, which is incorporated by reference as if set forth fully herein. The microfluidic device creates a highly ordered cell stream of controlled density within the imaging field of view ("FOV") of the LUCAS platform. This ordered cell stream will then be rapidly imaged (within <1 sec) over an ultra-large FOV of ~18 cm$^2$ using lens-less holographic imaging using a LUCAS platform. Captured diffraction signatures or cell holograms can be rapidly processed to quantify the heterogeneous solution of interest. The next cycle of imaging will be done after all the cells within the imaging FOV are removed.

Figure 11A:
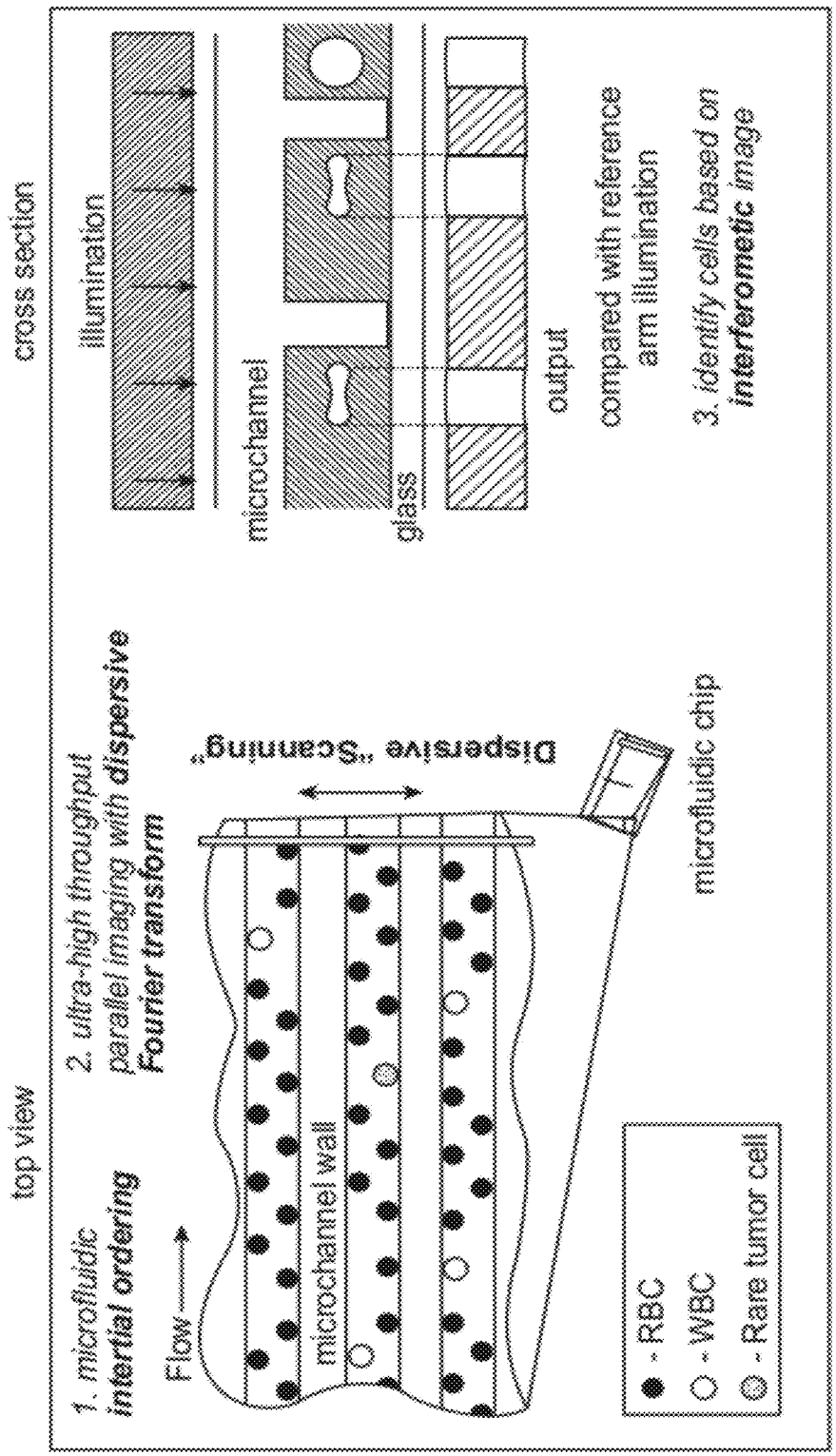
FIGS. 11a and 11b are schematic overviews of the major components of (a) the 2D Serial Time-Encoded Amplified Microfluidic Cytometer (STEAM-C) and (b) 3D STEAM imaging flow cytometer.
Figure 11B:
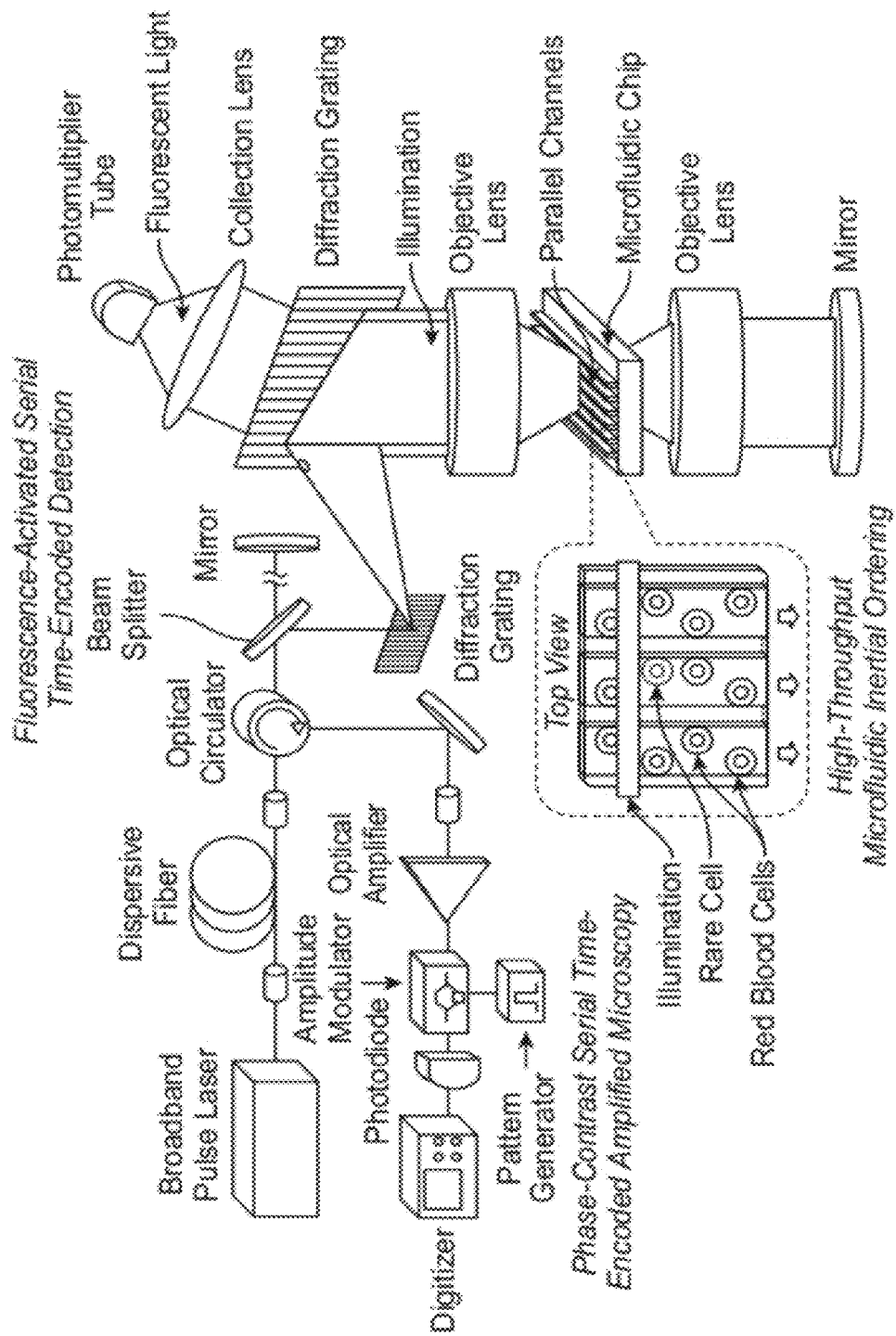

FIGS. 11a and 11b are schematic overviews of the major components of (a) the 2D Serial Time-Encoded Amplified Microfluidic Cytometer (STEAM-C) and (b) 3D STEAM imaging flow cytometer with the capability of fluorescent light detection. Details regarding STEAM methods may be found in Goda et al., Serial time-encoded amplified imaging for real-time observation of fast dynamic phenomena, Nature, 458, 1145-1149 (2009) which is incorporated by reference herein. Both systems include major components, such as (1) high-throughput microfluidic inertial ordering of blood cells in high-aspect ratio microchannels and (2) time to frequency domain transformation. 3D STEAM imaging flow cytometer has additional components, including (1) phase-contrast STEAM and (2) fluorescence-activated serial time-encoded detection.

FIGS. 12a-b are a flow chart (a) and a schematic (b) of operation of the system, including actuation in response to detected particle/cell characteristic. Optical detection can be conducted with a variety of approaches as discussed herein. Electrical detection can be conducted through measuring impedance or electrical opacity as described in *Microfluidic impedance-based flow cytometry*, Cheung, K. C., Di Berardino, M., Schade-Kampmann, G., Hebeisen, M., Pierzchalski, A., Bocsi, J., Mittag, A., Támok, A., *Cytometry A*. 2010, 77(7), 648-66, which is incorporated herein by reference. High-speed decision making and actuation includes selective optical or electrical lysis using hardware based image analysis using, e.g., FPGAs—field programmable gate arrays.

As summarized in FIG. 12a, the system first performs sheathless inertial focusing 36. FIG. 12b shows sheathless inertial focusing 36 through a series of parallel microchannels 14. Next, the system performs detection 38, which includes optical/electrical detection as shown in FIG. 12b. Then the system makes a decision 40 about the detected data through signal processing as shown in FIG. 12b. At this point, the system can provide feedback control 42 to the sheathless inertial focusing system to optimize the focusing, or stop flow to aid in actuation, sorting, or lysis. Finally, the system performs optical or electrical actuation 44 to separate the particles 18, as shown in FIG. 12b.

Uniform Velocity and z-Planes for Inertially-Ordered Particles.

As the channel 14 aspect ratio increases, particles 18 in rectangular microchannels 14 migrate predominantly to two lateral positions centered on the long channel faces (see FIGS. 6b and c). This phenomenon orders particles/cells into precisely controlled lateral and vertical positions. Inertial focusing of spherical polystyrene particles and sphered red blood cells was stable (i.e., uniform cell signature images and travel velocity) after achieving overall flow rates of Q=1.2 ml/min and 2.5 ml/min, respectively. These flow rates correspond to consistent particle Reynolds numbers of $R_p$=1.22 and 1.25, respectively.

However, inertial focusing of discoid red blood cells, both fresh and fixed, was not completely stabilized even at flow rates as high as Q=2.5 ml/min. Therefore, monodisperse polystyrene particles and sphered red blood cells were used for evaluating the massively parallel inertial microfluidic system functionality (FIGS. 1a-c). High-speed microscopic images were obtained at 2.5 cm downstream greater than the critical channel length, $L_f$ of 5 mm at the given flow rate (see FIG. 7), ensuring substantially complete particle ordering.

The average velocity of individual particles determined using manual image analysis was 0.208±0.003 m/s, which falls within 0.1% of average particle velocity obtained from automated image analysis of 0.208±0.004 m/s. FIG. 1c illustrates that precisely ordered particle 18 lattices travel through more than 200 parallel channels 14 with uniform velocity, $U_{ave}$=0.208 m/s (see FIG. 2).

Using inverted aspect ratio channels 14 (see FIG. 3a) as described in the methods, initially randomly distributed particles 18 form well-ordered particle trains 22 along the channel centerline (i.e., at the middle z-plane in our high aspect ratio channels 14). Lateral equilibrium positions of focused particles 18, $X_{eq}$, were determined by both manual and automated image analysis and results from both methods agreed well within 1.37±0.32 μm (see FIG. 8). FIGS. 3b and 3c illustrate the variation of particle focusing position in the z-direction as a function of channel Reynolds Number, $R_p$. Initially randomly distributed particles 18 began to migrate towards the channel centerline (i.e., a single z-plane, see FIG. 3a) as $R_p$ increased to 0.94. As the flow rate increased further ($R_p$>4.68), however, particles started to occupy more than one z-plane focusing position, indicating that there is an optimum flow rate for inertial focusing yielding a single z-plane in high-aspect ratio channels 14. Reynolds number dependence and changes in particle equilibrium positions have also been observed in Lattice-Boltzmann simulations of particle suspensions flowing through square ducts at high Reynolds number. Taking this data into account, focusing and analysis of blood cell populations was limited to a flow regime yielding $R_p$<4.68.

RBC and WBC Counts.

The inertial ordering system's features, i.e., (i) uniform z-heights and (ii) velocities, provide accurate optical cell identification of RBCs and WBCs in blood without staining. This application was assisted by the abovementioned automated MATLAB image analysis script to distinguish between RBCs and WBCs. Consequently, only large WBC types: neutrophils, eosinophils, basophils, and monocytes, were able to be identified as the detection of each the RBC and WBC types were based on visually distinguishable bright-field cell signatures (FIGS. 4a and b). At the operational flow rate of 2.5 ml/min, ($R_p$=1.25), with a field-of-view of 10 of the 256 channels 14, the ratio of the partial WBC population to RBCs and the sensitivity and specificity of RBC and WBC detection was analyzed and determined. The results are presented in the table in FIG. 5. The total count of n=7994 RBCs and n=24 WBCs, resulting in a ratio of 0.25% WBC to RBC, is within the same order of magnitude to the WBC to RBC ratio determined by the manually reviewed blood smear control (0.10%). Both automated and control samples agree well with reported literature values (0.07~0.23%). Regarding the cell detection algorithm, the false-positives, i.e., incorrect identification (<3% for RBCs and <12% for WBCs) is largely attributed to systematic errors such as defects in channel walls, and cell clumping. Whereas the false-negatives, cells evading detection, (<6% for RBCs and <14% for WBCs) is contributed by an incomplete sphering process, or low cell image contrast due to cell membrane leakage.

Parallel inertial ordering and focusing provide uniform cell conditions for optical interrogation. These uniform conditions increase automated cell identification accuracy in systems with focused cells compared to the same system with cells that were unfocused due to a reduced flow rate of 50 μL/min ($R_p$=0.02). At this low flow rate, the uniform array and focusing is lost and the cells are randomly dispersed throughout the z-plane as seen in z-plane measurements (compare FIGS. 4c and d). There is also a high incidence of cell-cell overlap in unfocused systems (see FIG. 4d). These factors significantly lower detection ability to differentiate between RBCs and WBCs (FIG. 4e). The randomly dispersed out-of-plane cells evade detection and cell type identification due to a blurred cell signature. In addition cell-cell overlap is a cause for undercounting and in some cases misidentification due to a false cell signature.

Although the above-described CBC system's accuracy and cell type differentiation capabilities fall short of the more complex and expensive commercial hematology analyzers, this system utilizes bright-field microscopy as its only interrogation method. Simplicity, ease of use, and robustness of automated enumeration and differentiation of cell types with an acceptable accuracy is achieved in this system. Future integration with next-generation-wide-field imaging techniques based on diffraction pattern recognition can be readily implemented as patterns will be tightly controlled due to inertial focusing of cells to narrow focal plane and uniform velocities this system provides. Future increases in accuracy and degree of cell type differentiation can be expected to rival and surpass commercial hematology analyzers.

The high-throughput, sheath-free cell positioning device 10 described above can be integrated with next-generation, wide-field, optical imaging techniques for extreme throughput flow cytometry, leading to interrogation rates up to 1 million cell/s. Combining the device 10 with standard bright field high-speed microscopy with a 10 channel FOV, facilitates automated detection of RBCs and WBCs in blood with high sensitivity and specificity for each cell type. Similar results cannot be achieved with unfocused cells.

When this system is integrated with suitably large field-of-view imaging or interrogation methods, the throughput of the system is estimated to be as high as 2 million cells/s flowing 1% v/v diluted blood through 100 parallel microfluidic channels at an overall flow rate Q=2.5 ml/min Moreover, the throughput of the system can be further increased by increasing operating flow rates, currently limited by resolution and detection speed of conventional CCDs (charged-coupled devices), when the system is integrated with ultrafast real-time optical imaging technique with ultra-high frame rate (6.1 MHz). With the future implementation of larger FOV acquisition technologies new applications are possible, including fast total complete blood counts with limited logistical footprint, and statistically significant identification of rare cells enabled by the extreme throughput.

Potential Applications and System Integration

The sheathless inertial focusing system 10 can be utilized for applications that would require continuous enumeration, identification, and classification of bio-particles in body fluids (e.g., rare cells or bacteria in blood, urine, saliva, etc.) and undesirable particles in purified water during the water filtration. In addition, since the flowing particles are rotating at a high frequency (>10 kHz), high-speed sequential parallel imaging enables three dimensional morphological studies of flowing particles (e.g., stained white blood cells to observe nuclear morphology, and micro-organisms in seawater or freshwater).

The simplicity of system allows easy integration with various current detection techniques (e.g. focused laser, side illumination fluorescence spectroscopy and electrical impedance measurement), parallel imaging techniques (e.g., LUCAS (FIG. 10) and FAST), automated image processing techniques, decision making algorithm (e.g., field-programmable gate array (FPGA) (FIGS. 12a-b)) with fast feed-back control, and parallel optical actuating systems using spatial light modulators such as DLP®. For example, the sheathless inertial focusing system integrated with fast feed-back control can be used in situ quality control (or on-line monitoring) of micro-particle synthesis process. Instant UV polymerization of inertially focused particle lattices will enable the fabrication of meta-materials with precisely controlled void size and spacing for photonic and acoustic applications. FAST is fiber-optic array scanning technology described in *High speed detection of circulating tumor cells*, Hsieh, H. B., Marrinucci, D., Bethel, K., Curry, D. N., Humphrey, M., Krivacic, R. T., Kroener, J., Kroener, L., Ladanyi, A., Lazarus, N., Kuhn, P., Bruce, R. H., Nieva, J., *Biosens Bioelectron,* 2006 Apr. 15, 21(10), 1893-9, which is incorporated herein by reference.

While embodiments have been shown and described, various modifications may be made without departing from the scope of the inventive concepts disclosed herein. The invention(s), therefore, should not be limited, except to the following claims, and their equivalents.

What is claimed is:

1. A flow cytometry system, comprising:
   an inertial particle focusing device comprising a plurality of substantially parallel microchannels formed in a substrate, each microchannel having a width to height ratio in the range of 2:3 to 1:4;
   an analyzer disposed adjacent the inertial particle focusing device such that the analyzer is configured to detect a characteristic of particles in the inertial particle focusing device; and
   a controller connected to the analyzer and configured to direct the detection of the characteristic of the particles.

2. The system of claim 1, wherein the inertial particle focusing device further comprises:
   an inlet connected to the reservoir connected to a proximal end of each microchannel;

a reservoir containing particles in fluid and connected to the inlet; and an outlet connected to a distal end of each microchannel.

3. The system of claim 2, wherein the system includes a pressure source configured to drive the particles in fluid through the inertial particle focusing device.

4. The system of claim 2, wherein the inlet includes a filter.

5. The system of claim 1, wherein the plurality of substantially parallel microchannels comprises 10-1000 microchannels.

6. The system of claim 5, wherein the plurality of substantially parallel microchannels comprises approximately 250 microchannels.

7. The system of claim 1, wherein each microchannel is substantially rectangular in cross section.

8. The system of claim 1, wherein each microchannel has a width to height ratio of approximately 2:1.

9. The system of claim 1, wherein the analyzer is aligned with a short (x) axis of the microchannels.

10. The system of claim 1, wherein the analyzer is disposed relative to the microchannels such that the analyzer is configured to detect the characteristic of particles at a distal end of at least one microchannel.

11. The system of claim 1, wherein the analyzer has a field of view sufficiently large to simultaneously detect the characteristic of particles in at least 10 microchannels.

12. The system of claim 1, wherein each microchannel has width W and the system is configured for use with particles having diameter a, such that a is between 20% and 70% of W.

13. The system of claim 1, wherein each microchannel has width W and the system is configured for use with particles having diameter a suspended in fluid having density $\rho$, maximum velocity $U_m$, and viscosity $\mu$, such that particle Reynolds number, $R_p = \rho U_m a^2/\mu W$, is between 0.3 to 2.

14. The system of claim 1, wherein the characteristic is selected from the group consisting of an optical signature and an electrical signature.

15. The system of claim 1, wherein the analyzer is configured to capture an image of particles in the inertial particle focusing device.

16. A method of analyzing particles, comprising:
suspending the particles in a fluid;
flowing the fluid and particles through an inertial particle focusing device including a plurality of substantially parallel, high-aspect ratio microchannels formed in a substrate, each microchannel having a width to height ratio in the range of 2:3 to 1:4;

detecting a characteristic of particles in the inertial particle focusing device; and analyzing the detected characteristic.

17. The method of claim 16, wherein each microchannel has width W, the particles have diameter a, and the fluid having density $\rho$, maximum velocity $U_m$, and viscosity $\mu$, such that particle Reynolds number, $R_p = \rho U_m a^2/\mu W$, is between 0.3 to 2.

18. The method of claim 16, wherein flowing the fluid and particles through an inertial particle focusing device substantially focuses the particles in a z direction.

19. The method of claim 16, wherein flowing the fluid and particles through an inertial particle focusing device substantially aligns the particles in an x direction.

20. The method of claim 16, wherein flowing the fluid and particles through an inertial particle focusing device substantially uniformly spaces individual particles in a y direction.

21. The method of claim 16, wherein detecting a characteristic of particles in the inertial particle focusing device comprises detecting the characteristic along a short (x) axis of the microchannel.

22. The method of claim 16, wherein detecting a characteristic of particles in the inertial particle focusing device comprises detecting the characteristic of particles at a distal end of a microchannel.

23. The method of claim 16, wherein detecting a characteristic of particles in the inertial particle focusing device comprises simultaneously detecting the characteristic of particles in portions of at least 10 microchannels.

24. The method of claim 16, wherein analyzing the detected characteristic comprises identifying at least two types of particles.

25. The method of claim 24, wherein identifying at least two types of particles comprises identifying visually distinguishable bright-field cell signatures.

26. The method of claim 16, wherein each microchannel has width W and the particles have diameter a, such that a is between 20% and 70% of W.

27. The method of claim 16, wherein the characteristic is selected from the group consisting of an optical signature and an electrical signature.

28. The method of claim 16, wherein detecting a characteristic comprises capturing an image of particles in the inertial particle focusing device.

* * * * *